(12) United States Patent
Kakuuchi (10) Patent No.: US 8,545,018 B2
(45) Date of Patent: Oct. 1, 2013

(54) OPHTHALMIC PHOTOGRAPHY APPARATUS (75) Inventor: Atsushi Kakuuchi, Hamamatsu (JP)

(73) Assignee: Kowa Company Ltd. (JP)

( * ) Notice: Subject to any disclaimer, the term of this patent is extended or adjusted under 35 U.S.C. 154(b) by 0 days.

(21) Appl. No.: 13/261,056

(22) PCT Filed: Jun. 5, 2009

(86) PCT No.: PCT/JP2009/060319
§ 371 (c)(1),
(2), (4) Date: Dec. 1, 2011

(87) PCT Pub. No.: WO2010/140246
PCT Pub. Date: Dec. 9, 2010

(65) Prior Publication Data
US 2012/0069300 A1 Mar. 22, 2012

(51) Int. Cl.
*A61B 3/14* (2006.01)
*A61B 3/10* (2006.01)
*A61B 3/02* (2006.01)

(52) U.S. Cl.
USPC .......................... 351/206; 351/214; 351/240

(58) Field of Classification Search
USPC ................... 351/205, 206, 214, 240; 396/28, 396/89, 91, 267, 335; 359/389; 348/E13.014
See application file for complete search history.

(56) References Cited

U.S. PATENT DOCUMENTS

2007/0132951 A1* 6/2007 Suzuki .......................... 351/206

* cited by examiner

*Primary Examiner* — Mahidere Sahle
(74) *Attorney, Agent, or Firm* — Adams & Wilks (57) ABSTRACT

Positioning control relating to a two-aperture stop necessary for stereoscopic photography can be performed accurately and securely using a simple, inexpensive, compact, and lightweight structure. The apparatus comprises a two-aperture stop (28) provided with two stop apertures (28a, 28b), and a shutter plate (302) for opening and closing one of the two stop apertures. The two-aperture stop (28) is moved so as to intersect with an optical axis so that in monocular photography the two-aperture stop is positioned in a first position in which the stop aperture (28b) is disposed substantially at the center of the optical axis and so that in stereoscopic photography it is positioned in a second position in which the two stop apertures (28a, 28b) are disposed off-center from the optical axis. A drive mechanism comprising a cam plate (303), a spring (304), and a rotary solenoid (301) is used to move the shutter plate (302) so as to close the stop opening (28a) of the two stop apertures in the first position and to open both of the two stop apertures (28a, 28b) in the second position.

8 Claims, 7 Drawing Sheets

OPHTHALMIC PHOTOGRAPHY APPARATUS

CROSS-REFERENCE TO RELATED APPLICATION

This application is a U.S. national stage application of International Application No. PCT/JP2009/060319 filed Jun. 5, 2009, and published in a non-English language.

TECHNICAL FIELD

The present invention relates to an ophthalmic photography apparatus for performing stereoscopic photography using two stop apertures that are disposed off-center from an optical axis in a photographic optical system.

BACKGROUND ART

Conventionally, as shown in, for example, following Patent Documents 1 through 4, various proposals have been made with respect to an ophthalmic photography apparatus in which a photographic stop formed of a two-aperture stop is disposed in a photographic optical system to perform stereoscopic fundus photography with a different parallax.

PRIOR ART DOCUMENTS

Patent Documents

Patent Document 1: Japanese Laid-open Patent Publication No. 2008-55010
Patent Document 2: Japanese Examined Patent Publication No. 1987-46170
Patent Document 3: Japanese Laid-open Utility Model Publication No. 1988-68302
Patent Document 4: Japanese Laid-open Patent Publication No. 1998-75932

SUMMARY OF INVENTION

Problems to be Solved

The stop mechanism disclosed in Patent Document 1 allows a two-aperture stop to be realized under a variety of conditions, but the mechanism is bulky and requires at least three drive means, and is disadvantageous in terms of cost and equipment space.

The mechanism disclosed in Patent Document 2 is provided with respectively independent one-aperture stop for use in monocular photography and two-aperture stop for use in stereoscopic photography. The stop plate is therefore moved over a large distance during the switchover, making the mechanism disadvantageous in terms of switchover time. In addition, the stop position depends on the rotational position of the rotary solenoid, making the mechanism disadvantageous in terms of positioning precision.

The mechanism disclosed in Patent Document 3 proposes a configuration in which a stopper is provided as a method to ensure the positioning precision in the mechanism disclosed in Patent Document 2, but problems arise with bouncing-induced vibrations of the stop plate when a high-speed switchover occurs in the mechanism using the stopper, and it is difficult to perform photography immediately after the switchover.

The stop mechanism disclosed in Patent Document 4 requires a positioning sensor, and two photographs are taken in order to obtain a pair of parallax images in stereoscopic photography in this mechanism, making the mechanism disadvantageous in terms of involuntary eye movement during fixation and miosis.

It is an object of the present invention to solve the aforementioned problems and to allow positioning control for a two-aperture stop necessary for stereoscopic photography to be performed accurately and securely using a simple, inexpensive, compact, and lightweight structure, particularly in a fundus camera (retina camera) configured to make it possible to simultaneously obtain images for stereoscope without a time lag.

Means for Solving the Problems

In order to solve the aforementioned problems, the present invention provides an ophthalmic photography apparatus in which stereoscopic photography is performed using two stop apertures that are disposed off-center from an optical axis of a photographic optical system within the photographic optical system, the apparatus comprising: a stop plate having two stop apertures; a shutter plate for opening and closing one of the two stop apertures; and a drive mechanism driven by a single drive source for moving the stop plate so as to intersect with the optical axis so that, in monocular photography, the stop plate is positioned in a first position in which one of the two stop apertures is disposed substantially at the center of the optical axis, and, in stereoscopic photography, it is positioned in a second position in which the two stop apertures are disposed off-center from the optical axis, and also for moving the shutter plate so as to close the remaining other aperture of the two stop apertures in the first position and to open both of the two stop apertures in the second position.

The drive mechanism includes a rotary solenoid as the single drive source, and urging means for bringing the stop plate into contact with a cam surface of a cam plate linked to a drive shaft of the rotary solenoid, the first and second positions of the stop plate being selected by selecting the angle of rotation of the cam plate by the drive of the rotary solenoid.

The shutter plate is linked coaxially with the cam plate to the drive shaft of the rotary solenoid, and the shutter plate is moved in accordance with the drive of the rotary solenoid so that the remaining other aperture of the two stop apertures is closed in the first position of the stop plate and both of the two stop apertures are open in the second position of the stop plate.

In the vicinity of the aperture of the stop plate an exit opening is provided for mounting thereon an end face of an optical fiber used in an alignment target light projection for adjusting the relative position of the photographic optical system and the eye to be examined.

Effect of the Invention

According to the aforementioned arrangements, using a drive mechanism driven by a single drive source allows the two stop apertures of the stop plate to be positioned in stereoscopic photography in a second position disposed off center from the optical axis to simultaneously take images for stereoscope without a time lag, and allows one of the two stop apertures to be positioned in monocular photography in a first position disposed substantially at the center of the optical axis, allowing also the shutter plate to be moved so as to close the remaining other aperture of the two stop apertures in the first position. This advantageously produces an excellent effect in which positioning control relating to the two-aperture stop necessary for stereoscopic photography can be performed accurately and securely using a simple, inexpensive, compact, and lightweight structure.

The drive mechanism can be realized by a simple, inexpensive, compact, and lightweight structure including a rotary solenoid as a single drive source, and urging means for bringing the stop plate into contact with the cam surface of the cam plate that is linked to the drive shaft of the rotary solenoid.

The shutter plate is linked coaxially with the cam plate to the drive shaft of the rotary solenoid. This allows the shutter plate to be moved so that the remaining other aperture of the two stop apertures is closed in the first position of the stop plate, and both of the two stop apertures are open in the second position of the stop plate, thus allowing positioning control related to the two-aperture stop necessary for stereoscopic photography to be performed accurately and securely.

In the vicinity of the aperture on the stop plate, an exit opening is provided for mounting thereon an end face of an optical fiber used in an alignment target light projection for adjusting the relative positions of the photographic optical system and the eye to be examined. This allows alignment target light projection to be performed without using a complicated optical system.

DETAILED DESCRIPTION OF THE INVENTION

In the following, the present invention will be described in detail with reference to the embodiments shown in the drawings. In the following, a fundus camera configured so as to be able to simultaneously obtain images for stereoscope is shown as an example of an ophthalmic photography apparatus.

Embodiment 1

Figure 1:
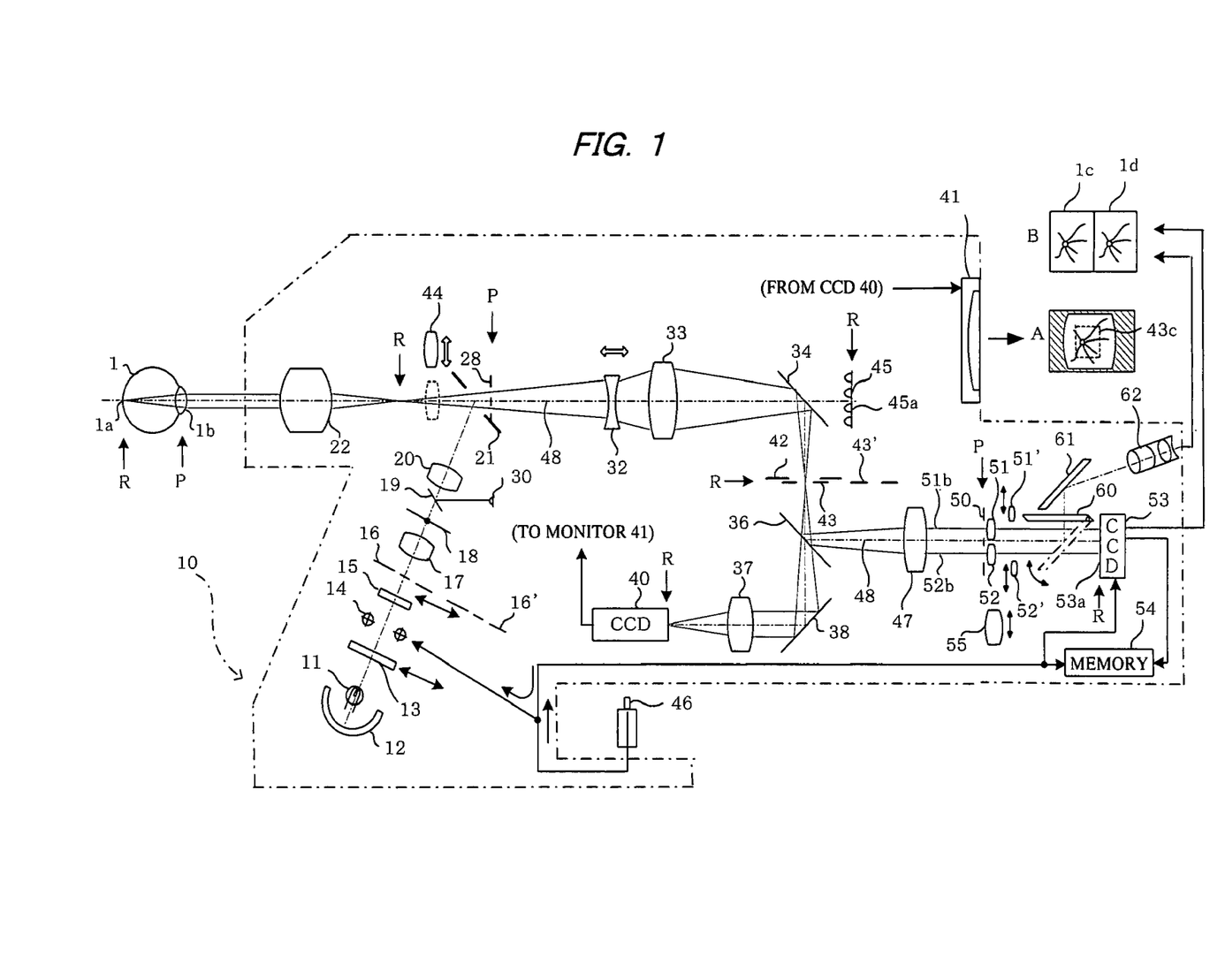
FIG. 1 is an optical diagram showing the configuration of an entire ophthalmic photography apparatus in which the present invention is employed.

FIG. 1 shows a fundus camera 10 capable of stereoscopic photography (three-dimensional photography) and monocular photography. The illustration in FIG. 1 is primarily that of stereoscopic photography, and a switchover to each corresponding optical element can be made when monocular photography is performed.

The fundus camera 10 is provided with an illumination optical system for illuminating the ocular fundus and an optical system for forming an image of the illuminated ocular fundus. In the illumination optical system, light emitted from a light source 11 such as a halogen lamp and light reflected by a concave mirror 12 is converted into infrared light via a visible-blocking/infrared-transmitting filter 13 that can be inserted into and removed from the optical path. The light then passes through a strobe 14 onto a diffusion plate 15 and is diffused thereon to illuminate a ring slit 16 for stereoscopic photography disposed in a position conjugate with an anterior ocular segment (pupil) 1b of an eye 1 to be examined. A switchover from the ring slit 16 to a monocular ring slit 16' can be made when monocular photography is performed.

Illuminating light passing through the ring slit 16 passes through a lens 17 and a black-spot plate 18 for removing the reflection from an objective lens 22, as well as through a half mirror 19 and a relay lens 20, and is reflected by an apertured total-reflection mirror 21 provided with an aperture in the center. The illuminating light reflected by the mirror 21 is incident through the objective lens 22 on the ocular fundus 1a via the anterior ocular segment 1b of the eye 1 to be examined to illuminate the ocular fundus 1a with infrared light.

The light reflected from the ocular fundus 1a is received via the objective lens 22, passes through the aperture in the apertured total-reflection mirror 21, and is incident on a two-aperture stop 28.

The two-aperture stop 28 is configured as shown in FIGS. 2a to 2d. The below-described FIG. 3 shows a photographic control procedure using the two-aperture stop 28.

Figure 2A:
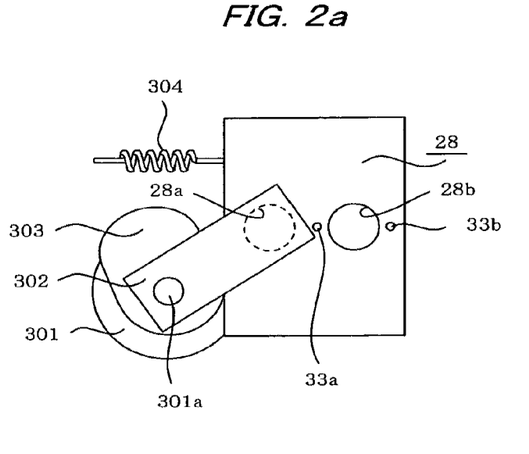
FIG. 2a is a rear view showing a two-aperture stop and a drive mechanism thereof as viewed from the back of a photographic optical system of the apparatus in FIG. 1.
Figure 3:
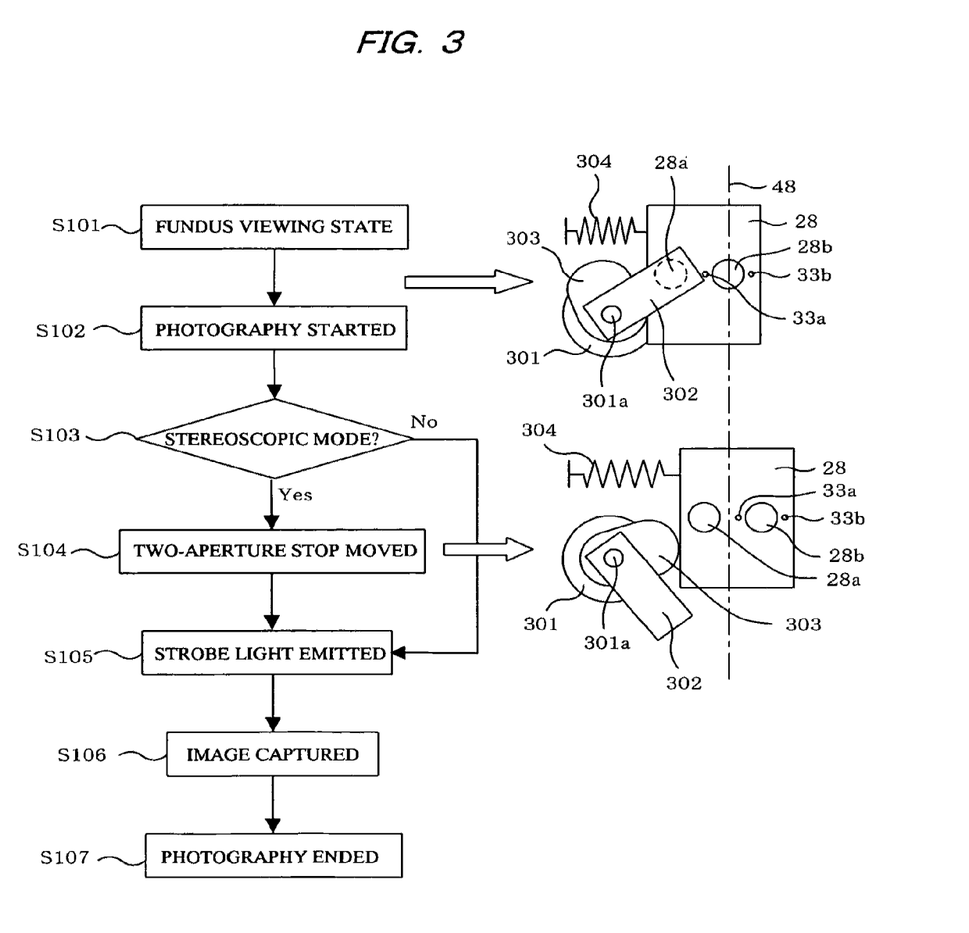
FIG. 3 is an illustrative view showing the photographic control procedure in the ophthalmic photography apparatus in FIG. 1.

As shown in FIG. 2a, a stop plate constituting a body part of the two-aperture stop 28 is provided with two circular apertures 28a, 28b and with exit openings 33a, 33b for mounting thereon an end face of an optical fiber of a target light projection system (not shown) used in an alignment target light projection for adjusting the relative positions of the photography apparatus and the eye to be examined. This allows alignment target light projection to be performed without using a complicated optical system. The stop plate constituting the body of the two-aperture stop 28 can be constructed of a metal plate or a resin plate.

The two-aperture stop 28 is disposed on an optical axis 48 of a photographic optical system in a position substantially conjugate with the anterior ocular segment (pupil) 1b of the eye to be examined. The position and size of the apertures 28a, 28b are set so that the aperture of the apertured total-reflection mirror 21 includes the entire apertures 28a, 28b.

The two-aperture stop 28 is supported via guiding means or the like (not shown) so as to intersect with the optical axis 48, and is driven by a drive mechanism using a rotary solenoid 301, a shutter plate 302, a cam plate 303, and a spring 304.

In the ocular fundus viewing mode or the monocular photography mode, the two-aperture stop 28 is moved so that the center of the aperture 28b coincides with the optical axis 48

(refer to FIG. 1) of the photographic optical system, as shown in the upper right of FIG. 3. At this time, the aperture 28a is closed by the shutter plate 302.

In the stereoscopic photography mode, the two-aperture stop 28 is moved so that the center position between the two apertures 28a, 28b coincides with the optical axis 48 (refer to FIG. 1) of the photographic optical system, as shown in the lower right of FIG. 3. At this time, the shutter plate 302 is offset from the two-aperture stop 28, as shown in the drawings, and both of the apertures 28a, 28b are in an open state. In the stereoscopic photography mode, the apertures 28a, 28b of the two-aperture stop 28 are off-center in relation to the optical axis 48 (FIGS. 1 and 3) and occupy bilaterally symmetric positions in relation to the optical axis 48.

Figure 2B:
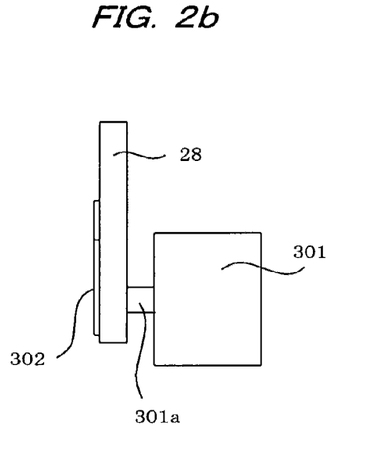
FIG. 2b is a side view showing a two-aperture stop and a drive mechanism thereof of a photographic optical system of the apparatus in FIG. 1.
Figure 2C:
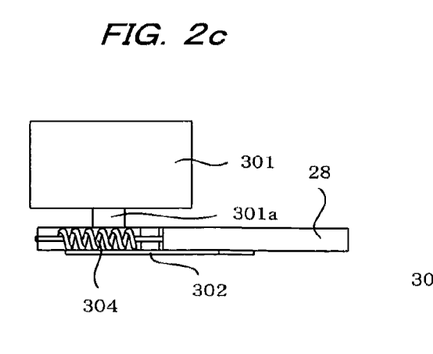
FIG. 2c is a top view of a two-aperture stop and a drive mechanism thereof of a photographic optical system of the apparatus in FIG. 1.
Figure 2D:
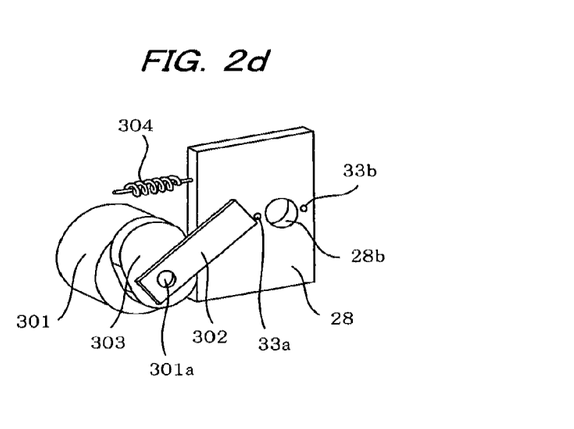
FIG. 2d is a perspective view of a two-aperture stop and a drive mechanism thereof of a photographic optical system of the apparatus in FIG. 1.

The drive mechanism of the two-aperture stop 28 will be described in more detail with reference to FIGS. 2a to 2d. FIG. 2a is a rear view showing the two-aperture stop 28 and the drive mechanism thereof as viewed from the back of the photographic optical system; FIG. 2b is a side view showing the two-aperture stop 28 and the drive mechanism thereof as viewed from the right side of FIG. 2a; FIG. 2c is a top view of the two-aperture stop 28 and the drive mechanism thereof; and FIG. 2d is a perspective view showing the two-aperture stop 28 and the drive mechanism thereof as viewed from the front left side of FIG. 2a.

The two-aperture stop 28 is usually urged leftward in the drawings by the spring 304. This causes an edge part of the two-aperture stop 28 in the left side of the drawings is brought into contact with the cam plate 303. The cam plate 303 has a substantially elliptical outside shape, as illustrated.

The cam plate 303 is linked to a drive shaft 301a of the rotary solenoid 301, and the shutter plate 302 is linked to the drive shaft 301a in a mutually coaxial relationship with the cam plate 303. Specifically, the rotary solenoid 301 constitutes a single drive source for the common coaxial driving of the cam plate 303 and the shutter plate 302.

Accordingly, the position of the two-aperture stop 28 can be controlled via the cam plate 303 by the rotary driving of the rotary solenoid 301, and the position of the shutter plate 302 can be controlled at the same time.

The shape of the cam plate 303 and the mounting angle of the cam plate 303 and the shutter plate 302 in relation to the drive shaft 301a is decided in advance so that the two-aperture stop 28 and the shutter plate 302 occupy the upper right positions in FIG. 2a and FIG. 3 in the ocular fundus viewing mode or the monocular photography mode, and the two-aperture stop 28 and the shutter plate 302 occupy the lower right positions in FIG. 3 in the stereoscopic photography mode.

In the stereoscopic photography mode, the two-aperture stop 28 is positioned (lower right of FIG. 3) by the below-described control so that the apertures 28a, 28b occupy positions that are off center on both sides of the optical axis 48, and the optical path of the light reflected from the ocular fundus is split to the right and left by the apertures 28a, 28b of the two-aperture stop 28. When the ocular fundus is viewed or a monocular photography is performed, the two-aperture stop 28 is positioned (upper right of FIG. 3) so that the center of the aperture 28b aligns with the optical axis 48.

Referring back to FIG. 1, a pair of right and left light beams from the ocular fundus 1a with the split optical path is incident on a focusing lens 32. The focusing lens 32 can move along the photographic optical axis to correct the deviation of the ocular fundus image-forming position caused by the individual differences in the diopter of the eye to be examined.

The ocular fundus image that has passed through the focusing lens 32 then passes through an image-forming lens 33, reflected by a half mirror 34, and made incident on an infrared-transmitting/visible-reflecting mirror (optical path splitting means) 36 via photographic masks 42, 43 that are disposed in a position conjugate with the ocular fundus 1a to determine a photographic range for the ocular fundus. In stereoscopic photography, the focusing lens 32 and the image-forming lens 33 constitute a first image-forming optical system in which the pair of right and left ocular fundus images with a parallax obtained via the two-aperture stop 28 are formed as intermediate images at the position of the photographic mask 43.

Figure 5A:
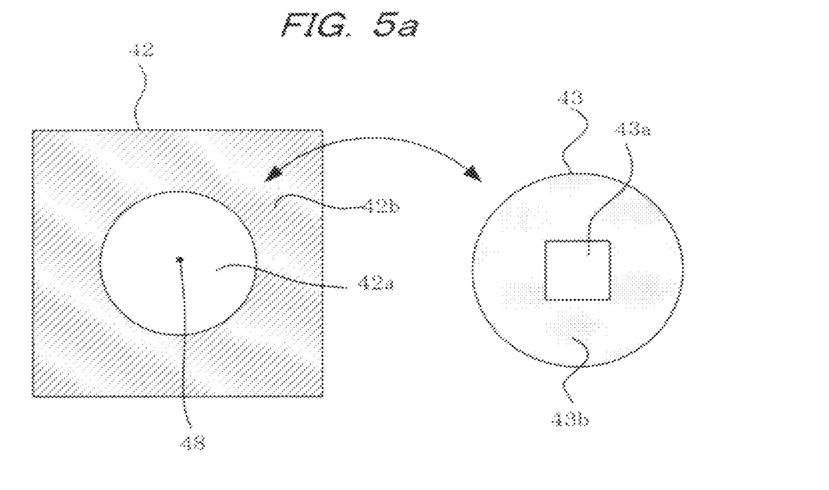
FIG. 5a is a front view separately showing a photographic mask for stereoscopic photography and monocular photography in the photographic optical system in FIG. 1.
Figure 5B:
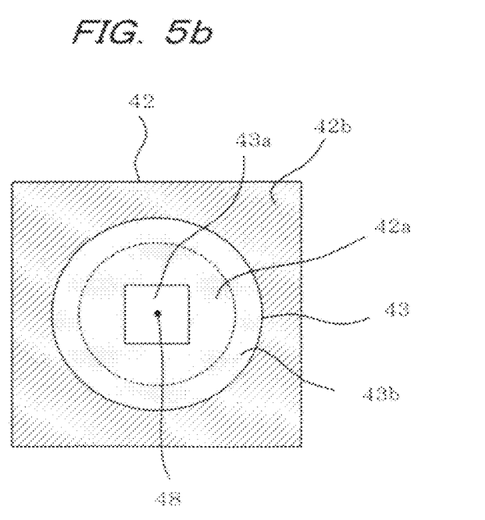
FIG. 5b is a front view of a photographic mask for stereoscopic photography and monocular photography disposed in an overlapping manner in the photographic optical system in FIG. 1.

The photographic mask 42 is, as shown in FIG. 5a, a photographic mask for monocular photography formed of a circular opening part 42a and a light-shielding part 42b that is non-transmittable to all wavelengths. The photographic mask 43 is a photographic mask for stereoscopic photography, and is constructed of a rectangular opening part 43a and a region 43b that has a circular periphery and is transmittable to only infrared light. The photographic mask 42 is fixedly disposed in the optical path in a manner in which the center of the mask coincides with the photographic optical axis 48. When stereoscopic photography is performed, the photographic mask 43 is inserted into the optical path so that the center of the mask coincides with the photographic optical axis 48, as shown in FIG. 5b. When monocular photography is performed, the photographic mask 43 is, as shown in FIG. 5a, removed from the optical path to activate the photographic mask 42.

Referring again to FIG. 1, the infrared light passing through the infrared-transmitting/visible-reflecting mirror 36 is reflected by a mirror 38, passes through a lens 37, and made incident on an imaging element (imaging means) 40 such as an infrared CCD sensitive to infrared light, and the signal therefrom is inputted to a monitor 41.

A relay lens 47 is disposed in order to form the image of the exit pupil in the first image-forming optical system on a second image-forming optical system (described below). Visible light reflected by the mirror 36 is incident via the relay lens 47 on a two-aperture stop 50 that is disposed in a position conjugate with the anterior ocular segment 1b. The two-aperture stop 50 is a stop similar to the stop plate of the two-aperture stop 28 as shown in FIGS. 2a to 2d. The two-aperture stop 50 is withdrawn from the optical axis 48 in the monocular photography or ocular fundus viewing mode, and is inserted into the optical axis 48 when stereoscopic photography is performed. A pair of optical path splitting lenses 51, 52 is disposed adjacent to the two-aperture stop 50 (that is, in a position substantially conjugate with the two-aperture stop 28). The pair of optical path splitting lenses splits the optical path from the photographic mask 43 as described below, and constitutes the second image-forming optical system in which the pair of right and left ocular fundus images formed as intermediate images at the position of the photographic mask 43 is re-formed so that they are separated into the right and left and do not overlap with each other. In this arrangement, the optical path splitting lenses 51, 52 are preferably disposed at equal intervals in relation to the photographic optical axis 48, that is, in axial symmetry in relation to the photographic optical axis 48.

An imaging plane 53a of an imaging element (imaging means) 53 such as a visible CCD sensitive to visible light is disposed on an image-forming plane in the second image-forming optical system. A return mirror 60 is disposed between the optical path splitting lenses 51, 52 and the imaging element 53. The separated pair of right and left ocular fundus images can be observed with the naked eye using an eyepiece lens (binocular viewing means) 62 via a mirror 61 in cases in which the visible-blocking/infrared-transmitting filter 13 is withdrawn from the optical path and the return mirror 60 is inserted into the optical path.

The ocular fundus image taken by the imaging element 53 can be stored in a memory 54 and loaded into an external computer (not shown), displayed on a monitor 41, or outputted to a printer (not shown).

A switchover can be made from the pair of optical path splitting lenses 51, 52 having the same magnification to another pair of optical path splitting lenses 51', 52' having different magnifications. This allows a pair of ocular fundus images to be photographed at the different magnifications. In conjunction with this, a switchover can be made from the photographic mask 43 for stereoscopic photography to a photographic mask 43' having a different opening when a switchover is made to the pair of optical path splitting lenses 51', 52' having different magnifications.

When monocular photography is performed, an image-forming lens 55 for monocular photography is inserted into the optical path instead of the optical path splitting lenses 51, 52, and the two-aperture stop 50 is removed from the optical path.

A focus-dot light source 30 is provided to the illumination optical system, and a light beam from the light source 30 is made incident on the ocular fundus 1a via the half mirror 19. The examiner can bring the ocular fundus being examined into focus by observing the focus dot because the position of the focus dot varies in accordance with the movement of the focusing lens 32.

In the initial alignment step, the insertion of an anterior ocular segment lens 44 allows the examiner to confirm the image of the anterior ocular segment 1b of the eye 1 to be examined on the monitor 41. Any of the LED light sources of internal fixation lamps 45 formed of a plurality of LED light sources 45a is turned on during alignment and focusing, and the examiner can accurately perform alignment and focusing by having the subject concentrate on the fixation lamp.

Figure 4:
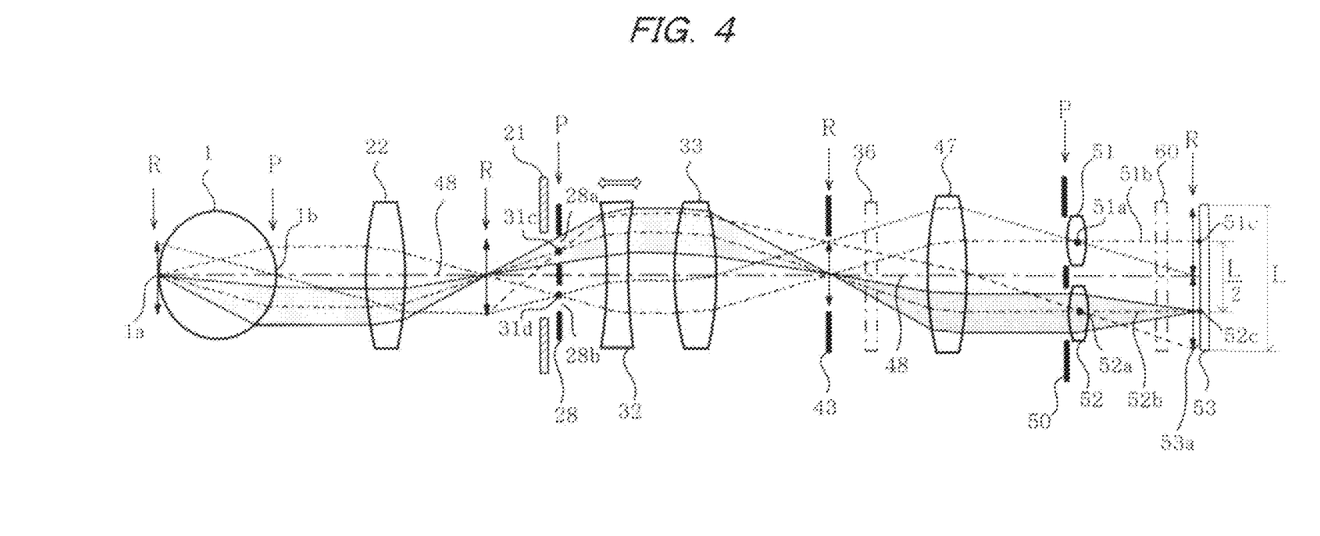
FIG. 4 is an optical diagram showing a fundamental optical configuration when performing stereoscopic photography by the photographic optical system in FIG. 1.

FIG. 4 shows the principal part of the optical system for forming an image of an ocular fundus when stereoscopic photography is performed. The same symbols are applied to elements that are the same as in FIG. 1.

The position conjugate with the ocular fundus 1a of the eye 1 to be examined is shown as R in FIGS. 1 and 4, and the position conjugate with the anterior ocular segment (specifically, the pupil) is shown as P.

The two-aperture stops 28, 50 and the optical path splitting lenses 51, 52 in FIGS. 1 and 4 are illustrated so that the optical path is split into top and bottom parts in the drawings, but the path is actually split to the right and left (in the direction perpendicular to the plane of the paper). However, it is difficult to illustrate a state in which the light beams are split to the right and left on the plane of the drawing, and the two-aperture stops 28, 50 and the optical path splitting lenses 51, 52 in FIGS. 1 and 4 are therefore illustrated as when seen from a direction orthogonal to the plane of the paper as a matter of convenience.

The operation of the ocular fundus camera thus configured will be described next with reference to FIG. 3. A summary of the stereoscopic photography or monocular photography of an ocular fundus of an eye to be examined in the afore-described configuration will be described below with reference to the flowchart on the left side of FIG. 3. The flowchart on the left side of FIG. 3 shows a summary of the photographic control procedure in the ocular fundus camera of the present embodiment.

In the ocular fundus camera thus configured, the alignment and the ocular fundus viewing mode (step S101) are established prior to ocular fundus photography. At this time, the visible-blocking/infrared-transmitting filter 13 is inserted into the illumination optical path, and the ocular fundus is therefore illuminated by infrared light when the halogen lamp 11 is turned on.

In the ocular fundus viewing mode, the rotational position of the rotary solenoid 301 is selected as shown on the upper right of FIG. 3 in order to position the two-aperture stop 28 so that the center of the aperture 28b coincides with the optical axis 48 (refer to FIG. 1) of the photographic optical system. At this time, the aperture 28a is closed by the shutter plate 302. The ring slit 16' and the image-forming lens 55 for monocular photography are inserted into the optical path. The photographic mask 43, the two-aperture stop 50, and the like are controlled so as to be withdrawn from the optical path. These states are similarly maintained in the case of monocular photography as well.

The ocular fundus image illuminated by infrared light is formed at the position of the photographic mask 42 by the objective lens 22, the focusing lens 32, and the image-forming lens 33. The fundus image is then transmitted through the infrared-transmitting/visible-reflecting mirror 36, and re-formed as a moving image on the imaging plane of the imaging element 40 by the image-forming lens 37. The ocular fundus image can therefore be displayed as a black-and-white image on the monitor 41, and observed in a non-mydriatic mode by the examiner via the monitor 41. At this time, the magnification of the image formed on the imaging element 40 is made less than the magnification of the image formed by the second image-forming optical system. This allows a wide-angle ocular fundus image to be observed, making an alignment easy in the non-mydriatic mode. The ocular fundus of the eye to be examined can also be brought into focus by observing focus dots produced by the light source 30.

In the initial steps of alignment, the examiner observes and aligns an image of the anterior ocular segment 1b of the eye 1 to be examined on the monitor 41 because of the insertion of the anterior ocular segment lens 44.

Prior to photography, the examiner determines via an operation means (not shown) whether either of photographic operations of the stereoscopic photography mode and the monocular photography mode is carried out. Upon completion of alignment, the actual photographic operation is started (step S102). At this time, in cases in which the stereoscopic photography mode is selected, the state of each part of the photographic optical system is switched from the state of alignment and ocular fundus viewing mode (step S101) to stereoscopic mode (steps S103, S104).

In cases in which the stereoscopic photography mode is set, the rotational position of the rotary solenoid 301 is selected as shown in the lower right of FIG. 3, and the two-aperture stop 28 is moved so that the center position between the two apertures 28a, 28b coincides with the optical axis 48 (refer to FIG. 1) of the photographic optical system. The shutter plate 302 is offset from the two-aperture stop 28 as shown in the drawing, and both of the apertures 28a, 28b are brought to an open state. In the stereoscopic photography mode, the apertures 28a, 28b of the two-aperture stop 28 are off-center in relation to the optical axis 48 (FIGS. 1 and 3), and occupy bilaterally symmetric positions in relation to the optical axis 48.

In the case of the monocular photography mode, the states for the two-aperture stop 28 and other members used for stereoscopic photography (photographic mask 43 and two-aperture stop 50) are the same as in the ocular fundus viewing mode, and the ocular fundus can be photographed in these states.

A shutter switch 46 is then operated, and an operating signal from the shutter switch is inputted to the imaging element 53 and the memory 54. This causes the imaging element 53 to be actuated to initiate the process of taking a still image of the ocular fundus. That is, in synchronization with the operating signal of the shutter switch 46, a signal to emit light is transmitted from the imaging element 53 to the strobe 14, thereby causing the strobe 14 to emit light (step S105). The ocular fundus illuminated by the light emitted from the strobe 14 is photographed as a still image by the imaging element 53 (step S106).

The state of the optical system in the stereoscopic photography mode will be described in detail below.

When stereoscopic photography is performed, the ring slit 16 and the optical path splitting lenses 51, 52 are inserted into the optical path instead of the ring slit 16', and the image-forming lens 55. The photographic mask 43 and the two-aperture stop 50 are also inserted into the optical path.

The optical path of the light beam from the ocular fundus 1a is split into the right and left by the apertures 28a, 28b of the two-aperture stop 28. Images are formed at the position of the photographic mask 43 by the focusing lens 32 and the image-forming lens 33 as a pair of right and left intermediate images having a parallax, and the ocular fundus images are observed using the monitor 41. The pair of ocular fundus images formed at the position of the photographic mask 43 is overlapped and displayed as one ocular fundus image on the monitor 41 when the ocular fundus is in focus. When the ocular fundus is out of focus, the pair of ocular fundus images is offset and displayed as a double image. Accordingly, in this case, the focusing lens 32 is once again adjusted so as to remove the double image.

The region 43b of the photographic mask 43 is a region in which only infrared light can be transmitted, and the rectangular opening part 43a transmits all of the wavelengths of the light beam. A rectangular outline 43c corresponding to the rectangular opening part 43a is therefore displayed on the image taken by the imaging element 40 and displayed on the monitor 41, as illustrated by A in the upper right of FIG. 1. The examiner can thus confirm the size of the photographic range when stereoscopic photography is performed.

The pair of right and left ocular fundus images having a parallax photographed at the position of the photographic mask 43 passes through the relay lens 47 and the two-aperture stop 50, and is made incident on the optical path splitting lenses 51, 52.

The relay lens 47 is disposed so as to form the exit pupil image of the first image-forming lens 33 on the optical path splitting lenses 51, 52. That is, the optical path splitting lenses 51, 52 are disposed in a position substantially conjugate with the anterior ocular segment 1b of the eye to be examined via the relay lens 47. The image of one aperture 28a of the two-aperture stop 28 is formed in the vicinity of the optical path splitting lens 52, and the image of the other aperture 28b is formed in the vicinity of the optical path splitting lens 51. Accordingly, as shown in FIG. 4, there is an image-forming relationship (conjugate relationship) between each of the centers of the apertures 28a, 28b of the two-aperture stop 28 and the lens centers 52a, 51a of the optical path splitting lenses 52, 51.

Light rays 51b, 52b passing through the centers 51a, 52a of the optical path splitting lenses 51, 52 via the center of the photographic mask 43 reach points 51c and 52c of the imaging plane 53a. The distance between the reached points 51c, 52c is set to a length equal to substantially half the distance of the entire length L of the imaging plane 53a along the direction (vertical direction in FIG. 4) orthogonal to the photographic optical axis 48. Therefore, the ocular fundus image of the pair of right and left ocular fundus images formed by the optical path splitting lens 51 is formed separately on the upper half of the imaging plane 53a, and the ocular fundus image thereof formed by the optical path splitting lens 52 is formed separately on the lower half of the imaging plane 53a without a mutual overlap, making it possible to obtain ocular fundus images for three-dimensional viewing that efficiently uses the entire imaging plane 53a.

In FIG. 4, the path of the light ray drawn in thin dots show that the left image (lower part of FIG. 4) having a parallax is formed on the left side (lower part) of the imaging plane, and the right image is formed on the right side (upper part) thereof. This allows the images having a parallax to be obtained with the relationship between the right and left being matched without requiring a prism for transposing the right and left in the conventional manner.

The pair of right and left ocular fundus images having a parallax separated by the optical path splitting lenses 51, 52 can be observed in the eyepiece lens 62 via the mirror 61 when the visible-blocking/infrared-transmitting filter 13 is withdrawn from the optical path and the return mirror 60 is inserted into the optical path, as shown in FIG. 1. At this time, the observed ocular fundus images are a separated pair of right and left ocular fundus images 1c, 1d having a parallax, as shown by B in the upper right of FIG. 1, and the examiner can view the ocular fundus in three dimensions.

The shutter switch 46 is operated in cases in which imaging is performed by the imaging element 53. The return mirror 60 is withdrawn from the optical path, and the strobe 14 is made to emit light in synchronization with this operation. The separated pair of right and left ocular fundus images 1c, 1d having a parallax is obtained on the imaging element 53 by the emission of light from the strobe 14 without overlap such as that seen in B in FIG. 1. The pair of ocular fundus images thus obtained is stored in the memory 54, and can be recalled at a later date for three-dimensional viewing by a three-dimensional viewing apparatus.

As shown in FIG. 1, a switchover can be made from the pair of optical path splitting lenses 51, 52 to another pair of optical path splitting lenses 51', 52' having different magnifications. In this case, a pair of reduced or enlarged ocular fundus images having a parallax is photographed. At this time, a switchover is made from the photographic mask 43 to the photographic mask 43' having a reduced or enlarged opening in accordance with the magnification in conjunction with the switchover.

The two-aperture stop 50 disposed adjacent to the optical path splitting lenses 51, 52 can be configured using the lens barrel of each of the lenses 51, 52, and is therefore not always necessary.

The present embodiment is advantageous in that the aperture 28b, which is one of the apertures 28a, 28b of the two-aperture stop 28 for photographing an image having a parallax in the stereoscopic photography mode, is configured so as to double as a photographic stop when monocular photography is performed, and therefore provides a simple and inexpensive structure. Another advantage is that excess mounting space is not required in the fundus camera, and the apparatus can be made compact and lightweight because the stop plate moves only a small distance. In addition, the two-aperture stop 28 can be moved (the apertures can be switched) using the shutter plate 302 and the cam plate 303 linked coaxially with the drive shaft 301a of the rotary solenoid 301. In the monocular photography or ocular fundus viewing mode, the shutter plate 302 blocks the unnecessary stop aperture so that it doesn't reach the effective diameter of a created single-aperture stop. A single drive means (rotary solenoid 301) further allows the positioning control of the two-aperture stop 28 and the closing of unnecessary stop aperture to be performed accurately and securely.

Particularly, the elliptical cam plate 303 is used in the present embodiment. This allows the position of the shutter plate 302 and the stop plate of the two-aperture stop 28 to be controlled with precision even if there are some errors in the stop position of the rotary solenoid 301.

In addition, the position control of the two-aperture stop 28 and the movement mechanism of the shutter plate 302 for open and close the stop apertures are realized by the rotary solenoid 301, the cam plate 303, and urging means (spring 304). This makes it possible to maintain the necessary positioning precision without using locking means such as a stopper, and also makes it possible to photograph objects promptly without problems such as the bouncing-induced vibrations of the stop plate and without the need to set a waiting period even immediately after the movement of the two-aperture stop 28.

Embodiment 2

In the above-mentioned embodiment, the shutter plate 302 is linked to the drive shaft of the rotary solenoid 301 coaxially with the cam plate 303 for moving the stop plate 28. The stop plate 28 is moved so as to intersect the optical axis so that, in monocular photography, the stop plate is positioned in a first position in which one aperture (28b) of the two stop apertures 28a, 28b is disposed substantially at the center of the optical axis (upper right of FIG. 3), and, in stereoscopic photography, it is positioned in a second position in which the two stop apertures 28a, 28b are disposed off-center from the optical axis (lower right of FIG. 3). The shutter plate 302 is operated in accordance with the drive of the rotary solenoid 301 so that the aperture 28a of the two stop apertures 28a, 28b is closed in the first position (upper right of FIG. 3) of the stop plate 28 and so that both of the two stop apertures 28a, 28b are open in the second position (lower right of FIG. 3) of the stop plate 28.

The present invention is characterized in that a drive mechanism is used in which the cam plate 303 for moving the stop plate 28 and the shutter plate 302 for controlling the opening and closing of the stop apertures are driven by a single drive source (rotary solenoid 301). Therefore, the coaxial linking is not always necessary for the interlocking relationship between the cam plate 303 and the shutter plate 302.

In the present embodiment, an example is given for a drive mechanism in which the cam plate 303 for moving the stop plate 28 and a shutter plate 312 for controlling the opening and closing of the stop apertures are driven by a single drive source (rotary solenoid 301) without the use of coaxial linking. Sections that are not expressly shown in the drawings are assumed to be the same in the arrangement of the entire apparatus as those shown in FIGS. 1 to 5, and detailed descriptions thereof are omitted. In addition, members that are the same as or common to those in the above-mentioned Embodiment 1 are given the same symbols, and detailed descriptions thereof are omitted.

Figure 6A:
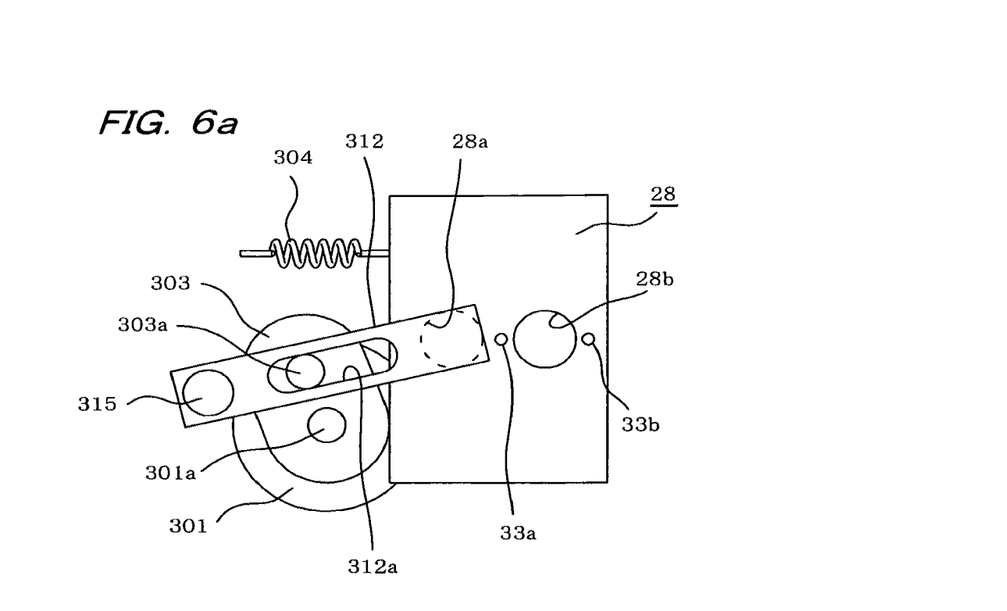
FIG. 6a is a rear view showing a two-aperture stop and a drive mechanism thereof as viewed from the back of a photographic optical system of the apparatus in FIG. 1.
Figure 6B:
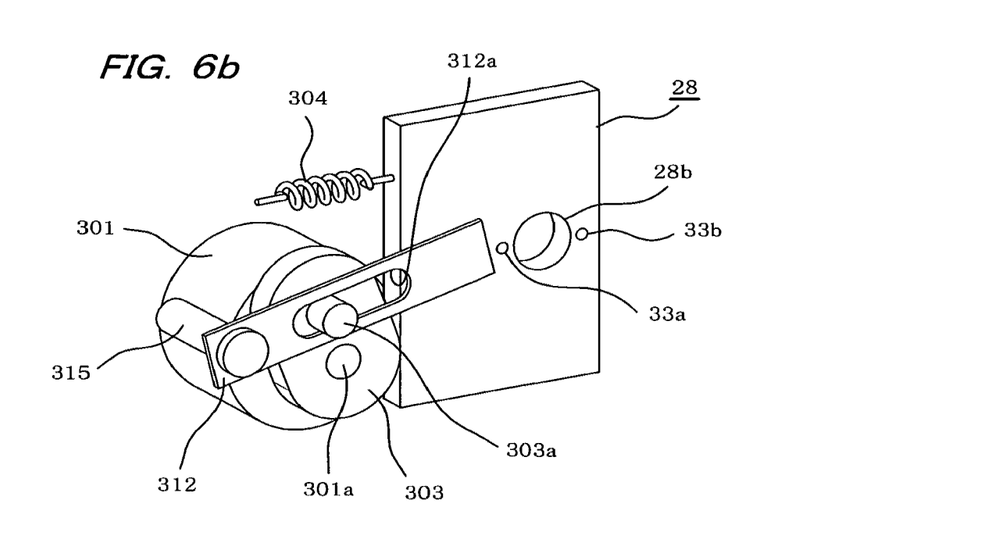
FIG. 6b is a perspective view of a two-aperture stop and a drive mechanism thereof of a photographic optical system of the apparatus in FIG. 1.

The drive mechanism of the two-aperture stop 28 of the present embodiment is configured as shown in FIGS. 6a and 6b. FIGS. 6a and 6b correspond to FIGS. 2a and 2b. FIG. 6a is a rear view showing the two-aperture stop 28 and the drive mechanism thereof, and FIG. 6b is a perspective view of the two-aperture stop 28 and the drive mechanism thereof.

Figure 7:
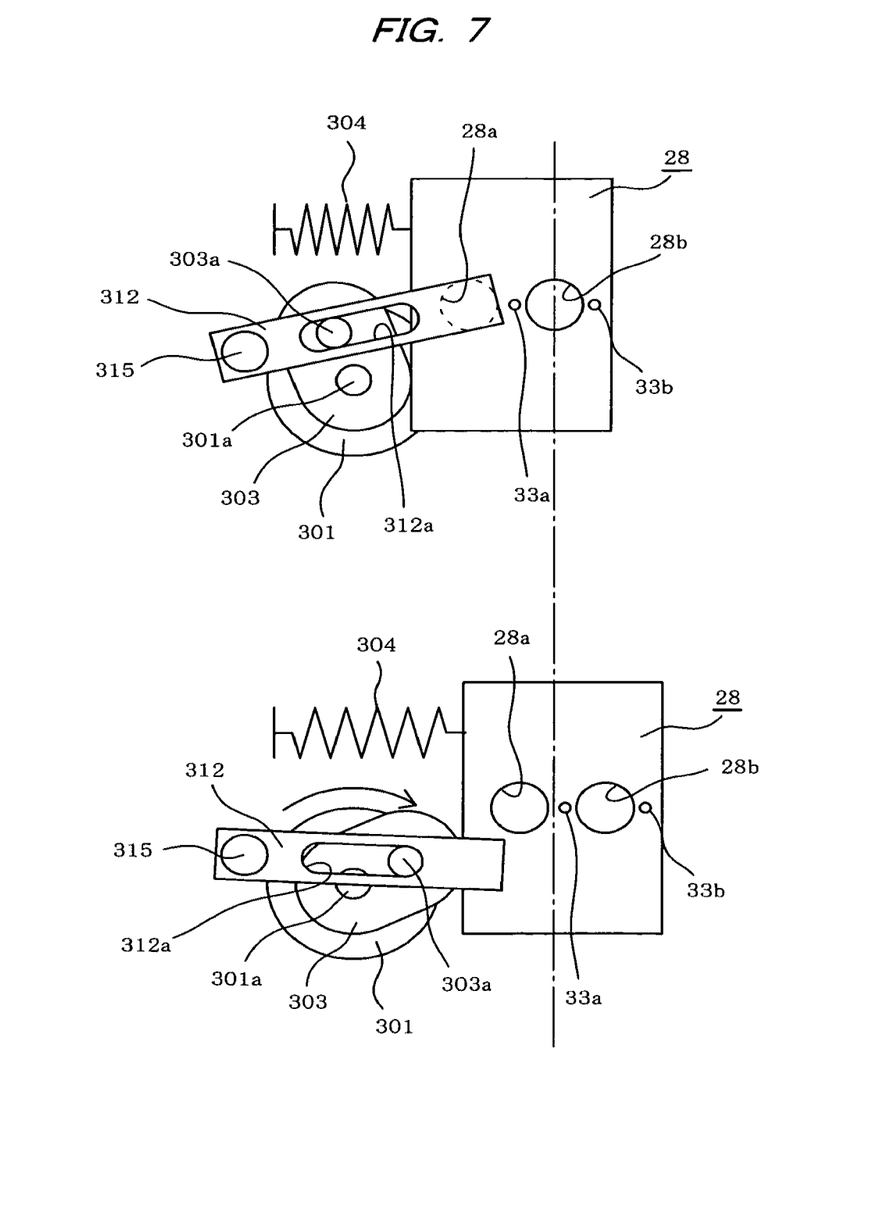
FIG. 7 is an illustrative view showing the operation of a two-aperture stop and a drive mechanism thereof of a photographic optical system of the apparatus in FIG. 1.

FIG. 7 is an illustrative view showing the operation of the drive mechanism of FIGS. 6a and 6b in the same form as that on the right side of FIG. 3. The flowchart section in FIG. 3 is omitted in FIG. 7, but the upper part of FIG. 7 shows the ocular fundus viewing state in, for example, steps S101, S102 in FIG. 3, or the state of the drive mechanism in the monocular photography mode, and the lower part of FIG. 7 shows the state of the drive mechanism in a case in which the stereoscopic photography mode is selected in, for example, step S103 of FIG. 3.

In the drive mechanism of the present embodiment, a shutter plate 312 is not rigidly linked to the drive shaft of the rotary solenoid 301, but is rotatably supported on a pivot shaft 315 provided in an appropriate position in the photographic optical system. A long hole or slot 312a is formed in the central portion of the shutter plate 312, and the long hole 312a is engaged with a pin 303a provided in the cam plate 303 having the same cam surface shape as that in Embodiment 1. In this manner, the shutter plate 312 is linked to the cam plate 303 through a pin-and-slot connection.

The shape of the cam plate 303, the position of the pivot shaft 315, the shape of the long hole 312a in the shutter plate 312, the position at which the pin 303a of the cam plate 303 is provided, and the like are determined in advance so that the two-aperture stop 28 and the shutter plate 312 occupy the position in FIG. 6a and the upper right of FIG. 7 in the ocular fundus viewing mode or the monocular photography mode, and so that the two-aperture stop 28 and the shutter plate 312 occupy the position in the lower right of FIG. 7 in the stereoscopic photography mode.

In the drive mechanism of the stop plate (two-aperture stop 28) thus configured, the cam plate 303 for moving the stop plate (two-aperture stop 28) and the shutter plate 312 for controlling the opening and closing of the stop apertures can be driven by a single drive source (rotary solenoid 301), and the cam plate 303 and the shutter plate 312 can be interlocked via the engagement of the long hole 312a of the shutter plate 312 with the pin 303a provided in the cam plate 303. The stop plate 28 can be moved so as to intersect the optical axis so that in monocular photography the stop plate is positioned in a first position in which one aperture (28b) of the two stop apertures 28a, 28b is disposed substantially at the center of the optical axis (upper right of FIG. 7) and so that in stereoscopic photography it is positioned in a second position in which the two stop apertures 28a, 28b are disposed off-center from the optical axis (lower right of FIG. 7). The shutter plate 312 can be moved so that the aperture 28a of the two stop apertures 28a, 28b is closed in the first position (upper right of FIG. 7) of the stop plate (two-aperture stop 28) and so that both of the two stop apertures 28a, 28b are open in the second position (lower right of FIG. 7) of the stop plate (two-aperture stop 28).

INDUSTRIAL APPLICABILITY

The present invention can be implemented in various ophthalmic photography apparatuses for performing stereoscopic photography using two stop apertures disposed off-center from an optical axis in a photographic optical system.

KEY TO SYMBOLS

1 Eye to be examined
21 Apertured total-reflection mirror
22 Objective lens
28 Two-aperture stop
31 Single-aperture stop
32 Focusing lens
33 Image-forming lens 40 Imaging element
42, 43 Photographic mask
46 Shutter switch
47 Relay lens
50 Two-aperture stop
51, 52 Optical path splitting lens
53 Imaging element
55 Image-forming lens for monocular photography
62 Eyepiece
301 Rotary solenoid
302, 312 Shutter plate
303 Cam plate
304 Spring
315 Pivot shaft

The invention claimed is:

1. An ophthalmic photography apparatus in which stereoscopic photography is performed using two stop apertures that are disposed off-center from an optical axis of a photographic optical system within the photographic optical system, the apparatus comprising:
    a stop plate having two stop apertures, the stop plate being movable relative to the optical axis to a first position in which one of the two stop apertures is disposed substantially at the center of the optical axis for use as a stop aperture in monocular photography, and to a second position in which the two stop apertures are disposed off-center from the optical axis for use as a stop aperture in stereoscopic photography;
    a movable shutter plate for opening and closing one of the two stop apertures; and
    a drive mechanism driven by a single drive source for moving the stop plate to the first and second positions and also for moving the shutter plate so as to close the remaining other aperture of the two stop apertures when the stop plate is in the first position and to open both of the two stop apertures when the stop plate is in the second position.

2. An ophthalmic photography apparatus according to claim 1, wherein the drive mechanism includes a rotary solenoid as the single drive source, and urging means for bringing the stop plate into contact with a cam surface of a cam plate linked to a drive shaft of the rotary solenoid, the first and second positions of the stop plate being selected by selecting the angle of rotation of the cam plate by the drive of the rotary solenoid.

3. An ophthalmic photography apparatus according to claim 2, wherein the shutter plate is linked coaxially with the cam plate to the drive shaft of the rotary solenoid, and the shutter plate is moved in accordance with the drive of the rotary solenoid so that the remaining other aperture of the two stop apertures is closed in the first position of the stop plate and both of the two stop apertures are open in the second position of the stop plate.

4. An ophthalmic photography apparatus according to claim 3, wherein the stop plate is provided with an exit opening for mounting an end face of an optical fiber used in an alignment target light projection for adjusting the relative position of the photographic optical system and the eye to be examined.

5. An ophthalmic photography apparatus according to claim 2, wherein the stop plate is provided with an exit opening for mounting an end face of an optical fiber used in an alignment target light projection for adjusting the relative position of the photographic optical system and the eye to be examined.

6. An ophthalmic photography apparatus according to claim 2, wherein the shutter plate is linked to the cam plate through a pin-and-slot connection.

7. An ophthalmic photography apparatus according to claim 1; wherein the stop plate is provided with an exit opening for mounting an end face of an optical fiber used in an alignment target light projection for adjusting the relative position of the photographic optical system and the eye to be examined.

8. An ophthalmic photography apparatus according to claim 1, wherein the stop plate has only two stop apertures.

* * * * *